United States Patent [19]
Frantz et al.

[11] Patent Number: 5,947,724
[45] Date of Patent: Sep. 7, 1999

[54] ELASTIC MANDIBULAR ADVANCEMENT APPLIANCE WITH SLIDE-IN BITE PLANES

[76] Inventors: Don E. Frantz, 400 Medical Center Blvd., #209, Webster, Tex. 77598; Michael D. Frantz, 1019 Foster, Couer d'Alene, Id. 83814

[21] Appl. No.: 08/841,851

[22] Filed: May 5, 1997

Related U.S. Application Data

[63] Continuation-in-part of application No. 08/493,926, Jun. 23, 1995.

[51] Int. Cl.⁶ ..................................................... A61C 3/00
[52] U.S. Cl. .................................. 433/19; 433/6; 433/24; 128/848; 128/861
[58] Field of Search .................................. 433/6, 19, 24; 128/848, 854, 861, 862

[56] References Cited

U.S. PATENT DOCUMENTS

| Re. 33,442 | 11/1990 | George | 128/860 |
| D. 302,036 | 7/1989 | George | D24/34 |
| 3,224,442 | 12/1965 | Stubbs | 128/136 |
| 3,536,069 | 10/1970 | Gores et al. | 128/136 |
| 4,169,473 | 10/1979 | Samelson | 128/136 |

(List continued on next page.)

FOREIGN PATENT DOCUMENTS 9428832  12/1994  WIPO .......................................... 5/56

OTHER PUBLICATIONS

Young, Terry, et al., The Occurence of Sleep–Disordered Breathing Among Middle Aged Adults, *The New England Journal of Medicine* (Apr. 29, 1993), vol. 328, No. 17, pp. 1230–1235.

Isono, Shiroh, et al., "Anatomy and Physiology of Upper Airway Obstruction" in *Principles and Practice of Sleep Medicine*, 2nd Edition, W.B. Saunders Company (1994), pp. 642–656.

Browman, Carl, et al., "Obstructive Sleep Apnea and Body Weight" in Chest (Mar., 1984), pp. 435–436.

Schmidt–Nowara, Wolfgang, et al., "Oral Appliances for the Treatment of Snoring and Obstructive Sleep Apnea: A Review" in Sleep, No. 6, vol. 18 (1995), pp. 501–510.

Lowe, Alan, "Dental Appliances for the Treatment of Snoring and Obstructive Sleep Apnea" in *Principles and Practice of Sleep Medicine*, 2nd Edition, W.B. Saunders Company (1994), pp. 722–735.

Clark, Glenn, et al., "The Effect of Anterior Mandibular Positioning on Obstructive Sleep Apnea", *Am.Rev.Respir..Dis.*, vol. 147 (1993), pp. 624–629.

W. Cassel, "Sleep Apnea and Personality", in Sleep, vol. 16, No. 8, (1993), pp. S56–S57.

Willy Chua et al., "Obstrucitve Sleep Apnea", in *Postgraduate Medicine*, Sleep Apnea, vol. 95/NO2 (Feb. 1, 1994).

Glenn T. Clark, et al., "Effect of Anterior Mandibular Positioning on Obstructive Sleep Apnea", A, Rev Res or Dos Vp; 147, pp. 624–629 (1993).

(List continued on next page.)

*Primary Examiner*—Nicholas D. Lucchesi
*Attorney, Agent, or Firm*—Browning Bushman

[57] ABSTRACT

A mandibular advancement, or positioning, device which uses elastic bands to pull the jaw forward is disclosed. The appliance has an upper base conforming to the patient's maxillary dentition soft tissue and palate, the upper base having a set of retention hooks, one on the right and one on the left anterior occlusal portion of the upper base. The appliance also has a lower base conforming to the patients mandibular dentition and soft tissues, the lower base having a set of interchangeable, slide-in posterior occlusal bite planes. These bite planes open the bite vertically in varying amounts depending on which bite plane is utilized, and also provide connection points for the elastic bands on the lower base. O-ring elastic bands or other elastics are attached to both the retention hooks and the bite planes hooks, to pull the mandible forward for treatment of snoring and sleep apnea.

25 Claims, 3 Drawing Sheets

U.S. PATENT DOCUMENTS

| | | | |
|---|---|---|---|
| 4,304,227 | 12/1981 | Samelson | 128/136 |
| 4,305,709 | 12/1981 | Bruhn et al. | 443/136 |
| 4,376,628 | 3/1983 | Aardse | 433/80 |
| 4,413,978 | 11/1983 | Kurz | 433/6 |
| 4,505,672 | 3/1985 | Kurz | 433/6 |
| 4,619,609 | 10/1986 | Clark | 433/6 |
| 4,715,368 | 12/1987 | George | 128/136 |
| 4,825,881 | 5/1989 | Bessler | 128/859 |
| 4,901,737 | 2/1990 | Toone | 128/848 |
| 4,986,283 | 1/1991 | Tepper | 128/859 |
| 5,003,994 | 4/1991 | Cook | 128/848 |
| 5,018,533 | 5/1991 | Hawkins | 128/848 |
| 5,046,512 | 9/1991 | Murchie | 128/848 |
| 5,082,007 | 1/1992 | Adell | 128/861 |
| 5,092,346 | 3/1992 | Hays | 128/848 |
| 5,117,816 | 6/1992 | Shapiro | 128/200.24 |
| 5,195,890 | 3/1993 | Johansson | 433/172 |
| 5,203,324 | 4/1993 | Kinkade | 128/201.11 |
| 5,267,862 | 12/1993 | Parker | 433/215 |
| 5,277,202 | 1/1994 | Hays | 128/848 |
| 5,313,960 | 5/1994 | Tomasi | 128/848 |
| 5,316,020 | 5/1994 | Truffer | 128/848 |
| 5,365,945 | 11/1994 | Halstrom | 128/848 |
| 5,409,017 | 4/1995 | Lowe | 128/848 |
| 5,443,384 | 8/1995 | Franseen et al. | 433/19 X |
| 5,499,633 | 3/1996 | Fenton | 128/848 |
| 5,562,106 | 10/1996 | Heeke et al. | 128/848 |
| 5,566,683 | 10/1996 | Thornton | 428/848 |
| 5,570,704 | 11/1996 | Buzzard et al. | 128/848 |
| 5,683,244 | 11/1977 | Truax | 433/6 |

OTHER PUBLICATIONS

Dr. George Cook, D.D.S., "Snoring and Sleep Apnea Questions/Answers A New Treatment Device", Compiled and Written by The Holdingford Dental Clinic (1990).

Scott E. Eveloff et al., "Effiacy of a Herbst manibular Advancement Device in Obstructive Sleep Apnea", *Am J Respir Crit Care med* vol. 149. pp. 905–909 (1994).

Peter T. George, D.D.S., "Treatment of Snoring and Obstructive Sleep Apnea with a Dental Device", *General Denistry*, pp. 294–298 (Aug. 1993).

Dr. Harry W. Tepper, "The Tepper Oral Proprioceptive Stimulator *, An Innovative Appliance Developed by Dr. Harry W. Tepper for the Treatment of Sleep Apnea and Chronic Snoring", Great Lakes Orthodonics, Ltd.

David R. Hillman, "Sleep Apnea and Myocardial Infarction", *Sleep*, vol. 16, No. 8, pp. S23–S24 (1993).

Poul Jennum, et al., "Cognitive Function and Snoring", *Sleep*, vol. 16, No. 8, pp. S62–S64 (1993).

Alan A. Lowe, "Can We Predict the Success of Dental Appliance Therapy for the Treatment of Obstructive Sleep Apnea Based on Anatomic Considerations?", *Sleep*, vol. 16, No. 8, pp. S93–S94 (1993).

H. Edward Lyon, D.D.S., "Treatment of Snoring and Obstructive Sleep Apnea", *Compend Contin Educ Dent*, vo. XIII, No. 5, pp. 416–420.

Robyn A. O'Sullivan et al, "Mandibular Advancement Splint: The Effects on Snoring and Obstructive Sleep Apnea", *Sleep*, vol. 16, No. 8, pp. S143 (1993).

Karen E. Shelton, et al., Adipose Tissue Deposition in Sleep Apnea, *Sleep*, vol. 16, No. 8, pp. S103–and A95 (1993).

Cohen, Robert B., DMD, "obstructive Sleep Apnea: A Mandibular Positioning Device for Treatment and Diagnosis of an Obstruction Site", *Compendium*, vo. 16, No. 6 pp.619–627 (Jun., 1995).

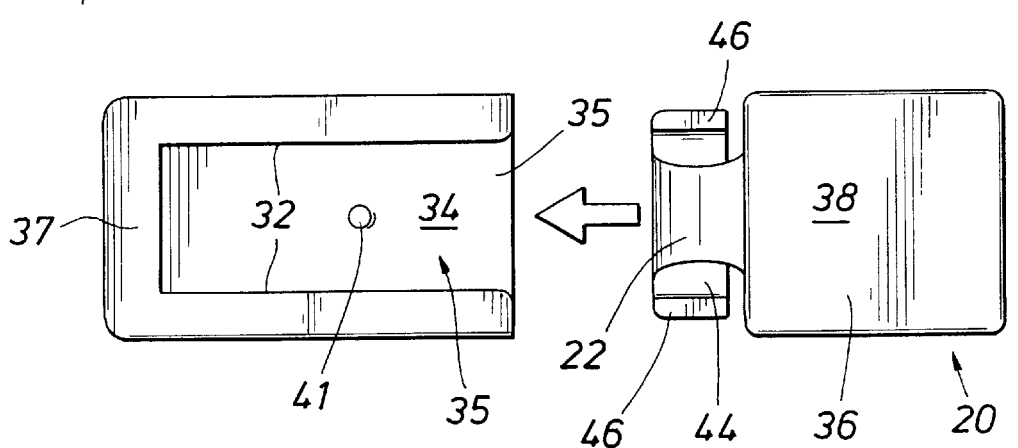
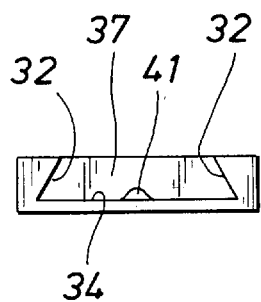 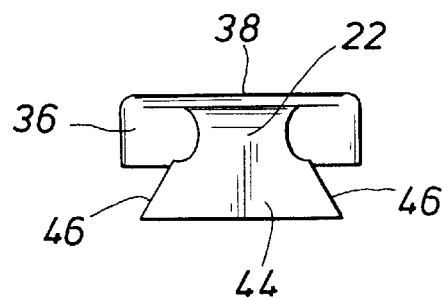
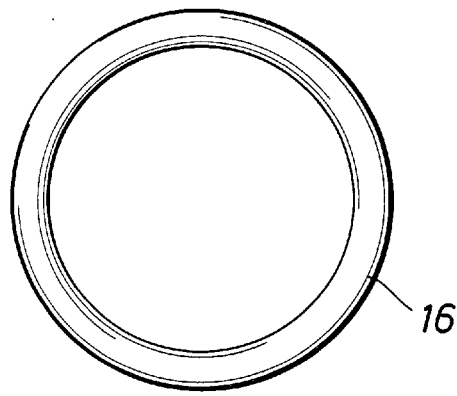 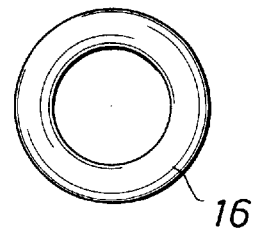

ELASTIC MANDIBULAR ADVANCEMENT APPLIANCE WITH SLIDE-IN BITE PLANES

This application is a continuation in part application of, and claims priority from, U.S. patent application Ser. No. 08/493,926, filed on Jun. 23, 1995, entitled "Elastic Mandibular Advancement Appliance", now abandoned, the disclosure of which is incorporated herein by this reference.

BACKGROUND OF THE INVENTION

1. Field of the Invention

This invention relates generally to oral appliances for preventing snoring and sleep apnea More specifically, this invention relates to a removable mandibular advancement appliance, which uses elastic bands to pull the jaw forward and removable, slide-in bite planes to open the bite vertically and to connect the elastic bands to the mandibular section of the appliance.

2. Related Art

It is well documented in the literature that an oral appliance that opens the bite and moves the mandible forward will greatly reduce sleep apnea and snoring. It is also documented that these appliances are capable of producing considerable discomfort to patients, unwanted movement of their teeth, and/or temporomandibular joint pain as well as other problems.

A variety of oral appliances are available for preventing snoring and sleep apnea. Of these, all are removable. Also, most advance the mandible, but none use elastic bands to move the mandible forward. Also, none use removable bite planes to variably open the jaw vertically.

Also, several removable, oral snoring/apnea appliances are adjustable, pulling the jaw forward in different, set percentages of their maximum movement. However, no known existing appliance is totally adjustable, both in amount of forward movement and vertical opening. Instead, temporary or permanent adjustments to appliances are made by either soldering spacers onto the appliance, or by grinding away plastic or other material from the appliance. Once modifications are made, however, they are permanent until further modified by the doctor. In summary, appliances exist in which the amount of advancement may be changed, but the changes result in a modified appliance which advances the mandible to a new fixed position.

What is needed is a totally adjustable, removable, oral snoring/sleep apnea appliance which is effective, which has high patient acceptance, and which will not cause temporomandibular joint problems, unwanted tooth movement or soreness. This need is satisfied by the present invention.

The objective of the appliance of the present invention is to greatly reduce, or eliminate, sleep apnea and snoring, while alleviating temporomandibular joint problems, unwanted tooth movement and soreness, with complete adjustability of the appliance both in the amount of forward movement of the lower jaw, and in the amount of vertical bite opening. Another object is a mandibular advancement appliance with high patient acceptance, comfort, and treatment success.

SUMMARY OF THE INVENTION

The present invention is a totally adjustable, removable, oral snoring/sleep apnea appliance. It is a mandibular advancement, or positioning, device which uses elastic members to pull the jaw forward relative to the jaw's natural biting position, and which uses removable, slide-in bite planes to vertically open the patient's bite.

The appliance has an upper section which comprises an upper base, herein also called "maxillary base", conforming to the patient's maxillary dentition, soft tissues and hard palate. The upper base has a set of retention hooks, one on the right and one on the left anterior occlusal portion of the base. Each retention hook extends downwardly from the upper base, in a position approximately corresponding to just in front of the cuspid teeth, for receiving the front portion of its respective elastic band or other elastic member.

The appliance of the present invention also has a lower section which comprises a lower base, herein also called "mandibular base" conforming to the patient's mandibular dentition, and soft tissues. The lower base has a set of preferably interchangeable, posterior occlusal bite planes, which serve as means for opening the patient's bite vertically and preferably also as means for connecting the elastic members to the lower base. The bite planes' top surfaces occlude with the posterior bottom surfaces of the upper base to distance the lower base from the upper base to open the bite. A front hook member or other extension of each bite plane receives the rear portion of its respective elastic member to connect the band to the mandibular section of the appliance.

The means for attaching the bite planes to the lower base preferably comprises sliding each bite plane into a channel in the posterior, top surface of the lower base. The channel is formed with a closed end and dove-tailed or other inwardly-extending walls to secure the bite plane to the lower base until the user or doctor chooses to remove the bite plane. The bite plane and channel are preferably also adapted to securely retain the elastic band until the bite plane is removed from the channel.

In use, the upper base is placed over the patient's maxillary dentition and the lower base is placed over the patient's mandibular dentition. With the chosen bite planes in place, each of the two elastic bands is extended from its respective lower base bite plane hook to its upper base retention hook. Thus, the lower base and mandible are elastically pulled forward relative to the upper base and maxilla and, hence, forward relative to the mandible's natural biting position. Thus, the upper and lower bases, and, hence, the maxilla and mandible are vertically separated to open the patient's bite.

Adjustability of vertical bite opening is achieved by providing different sets of bite planes, each set being designed to have a slightly different thickness for vertical openings of the bite ranging preferably from about 8–14 mm. Adjustability of the advancement of the mandible is achieved by providing different pairs of elastic bands, each pair having a slightly different length and different modules of elasticity. O-ring-shaped bands, urethane bands, standard orthodontic elastics, or other elastic bands may be used.

BRIEF DESCRIPTION OF THE DRAWINGS

FIG. 1 shows the side of the appliance corresponding to the patient's left side dentition, with the view of the right side of the appliance being generally a mirror image. The arrows in FIG. 1 illustrate the vertical opening of the upper and lower base due to the bite planes and the advancement of the lower base relative to the upper base.

FIG. 4 shows the bite plane of FIG. 2 being slid into the channel member of FIG. 2.

FIG. 5 shows a rear end view of the channel member of FIG. 2.

FIG. 6 shows a front view of the bite plane of FIG. 2.

FIG. 8 shows two relaxed O-ring elastic bands, of the type shown in FIG. 2, the bands having different diameters.

DESCRIPTION OF THE PREFERRED EMBODIMENTS

Figure 1:
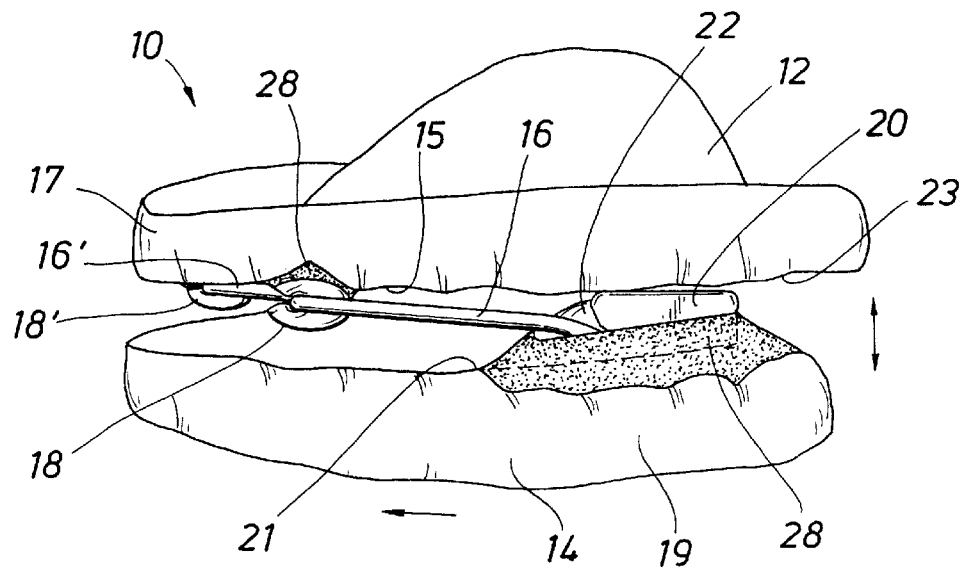
FIG. 1 is a side, perspective view of the upper and lower sections of one embodiment of the invention, showing upper and lower bases with the maxillary retention hooks and slide-in occlusal bite planes being connected with elastic bands.

Referring to the Figures, there are shown various, but not the only, embodiments of the invented elastic mandibular advancement appliance having slide-in bite planes. Depicted in FIG. 1 is an embodiment of the invention 10, showing the upper base 12 of the upper section, and the lower base 14 of the lower section connected with elastic bands 16, 16'. The bands 16, 16' extend from retention hooks 18, 18', which are located on the left and right occlusal surfaces 15 of the anterior portion 17 of upper base 12 near the upper cuspid teeth, to the bite planes hooks 22, 22' located at the front of the left and right bite planes 20, 20'. The preferably removable and interchangeable bite planes 20 slide in from the posterior portion 19 left and right occlusal surfaces 21 of lower base 14, near the lower molar teeth, to upend from the lower base to occlude with the posterior occlusal surface 23 of the upper base for vertically opening the user's bite.

Figure 2:
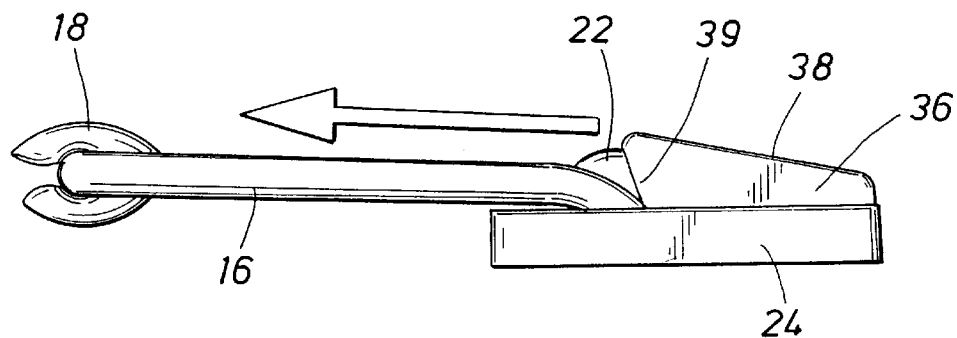
FIG. 2 is a detail view of the means for connecting the upper and lower bases of the embodiment of FIG. 1.

The preferred means for connecting the upper and lower bases and for vertically separating the upper and lower bases is detailed in FIG. 2. These means comprise the bite plane 20 slidably received in a channel 24 in the lower base, and the elastic band 16 received in and interconnecting the retention hook 18 and the bite plane hook 22. Thus, by elastically connecting the anterior portion of the upper base to the posterior position of the lower base, the right and left elastic bands may pull the bite planes 20, 20' forward in the channels 24 and may pull the lower base 14 forward relative to the upper base 12, and, hence, may advance the mandible. The invented appliance offers increased comfort for the patient, because no hooks or other protrusions need extend out from the buccal (side) areas of the appliance. Because the retention hooks and bite plane hooks are preferably at the occlusal portions of the upper and lower trays, respectively, the elastic bands are positioned nearly horizontally and there is a substantially horizontal component to the advancement and little or no vertical component to the advancement. For users who tend to naturally clench their teeth, this substantially horizontal force may be beneficial and may result in even more comfort for the patient.

Figure 3A:
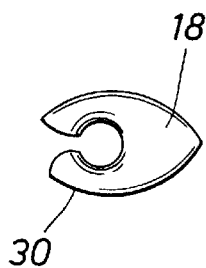
FIG. 3A shows a side view of the retention hook of FIG. 2.
Figure 3B:
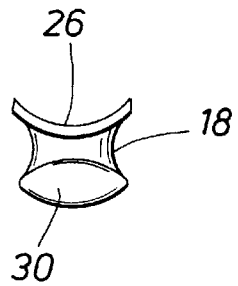
FIG. 3B shows a front view of the retention hook of FIG. 2.
Figure 7A:
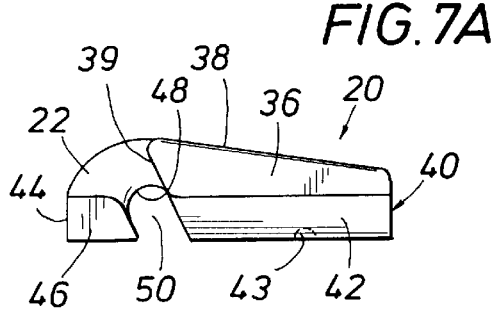
FIGS. 7A–G show side views of seven bite planes having different thickness, increasing from FIG. 7A to FIG. 7G in increments of approximately ½ mm.
Figure 7B:
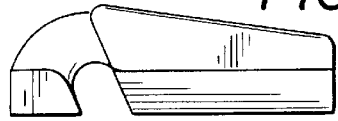
Figure 7C:
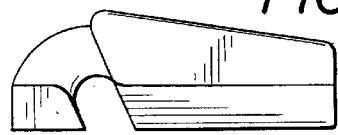
Figure 7D:
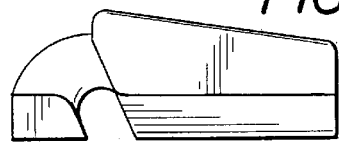
Figure 7E:
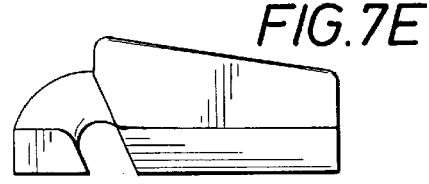
Figure 7F:
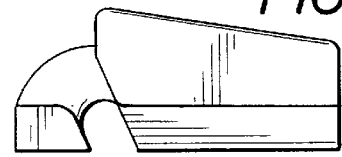
Figure 9:
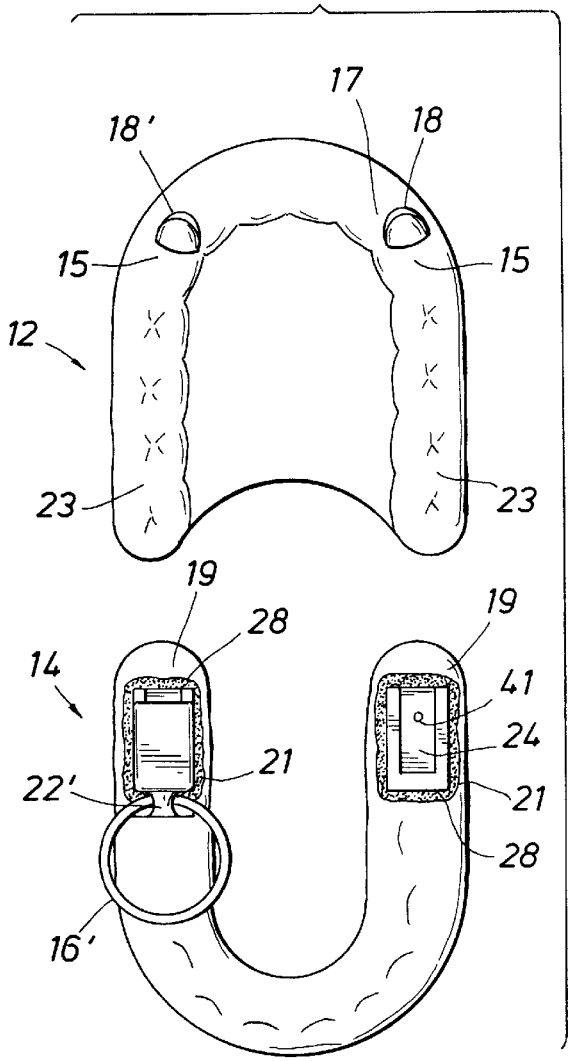
FIG. 9 shows the bottom surface of the upper base and the top surface of the lower base of the embodiment of FIG. 1, with the right bite plane in place and a relaxed right elastic band in the bite plane hook.
Figure 7G:
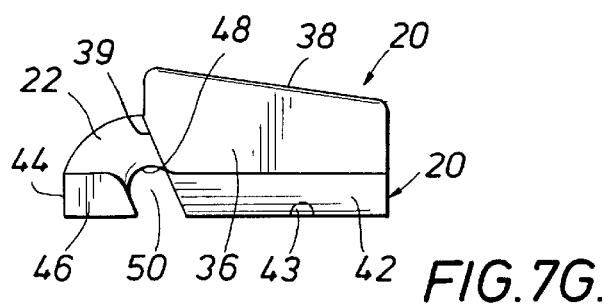

FIGS. 3A and 3B illustrate an embodiment of the maxillary retention hooks 18, 18' used in the present invention. The retention hooks 18, 18' are generally C-shaped hooks, with a concave upper surface 26 bonded by orthodontic acrylic 28 to the upper base 12 so that the arms of the hook point forward to receive an anterior portion or end of the elastic band 16. Two retention hooks 18, 18' are used, with one retention hook 18' being placed on the right anterior occlusal portion, and one retention hook 18 being placed on the left of the anterior occlusal portion, of the maxillary base. The lower arm 30 of each hook 18, 18' is sized to extend down from the upper base 12 far enough to receive and securely hold the elastic band 16, 16', but not so far as to interfere with the proper positioning of the upper and lower bases 12, 14. Alternatively, other retention hook or button designs may be used, including ones located on other anterior areas of the upper base.

In FIGS. 4–6 and 7A–G, there are depicted the preferred bite plane 20, and the channel 24 that lies longitudinally along the lower base posterior portion for receiving the bite plane. The channel 24 comprises generally dove-tailed channel sidewalls 32, a generally planar bottom wall 34, an open, back end, and a closed, front end. The bite plane 20 has a body 36 with a generally planar top occlusal surface 38 and a bottom anchoring portion 40 with sides 42 slanting inwardly to mate with the dove-tailed channel sidewalls 32. Thus, the bite plane 20 may slide into the channel 24 through the open end 35 and be retained securely in the channel 24 by the sidewalls 32, which prevent upward movement of the bite plane 20, and by the closed end 37, which prevents forward movement of the bite plane 20. The preferred channel sidewalls 32 prevent lateral movement of the bite plane on the lower base.

In order to prevent the bite planes 20, 20' from sliding out of the channels, in the event that an elastic band 16, 16' breaks during use, a safety means is preferably included. For example, a small protrusion 41 extending up from the channel bottom wall 34 may mate with a small recess 43 in the bite-plane anchoring portion 40, so that the bite plane "snaps" into place. This feature provides preferably enough resistance to keep the bite planes in place to eliminate danger of swallowing.

The bite plane hook 22 smoothly arches forward and down from a front side 39 of the body 36 of the bite plane 20, so that the hook 22 does not extend above the top occlusal surface 38 of the bite plane. The hook 22 has an outer end 44 with slanted sides 46 for being received and captured in the channel 24 in similar manner to the anchoring portion sides 42. Before sliding the bite plane 20 into the channel, a posterior portion or end of the elastic band 16 is placed around the bite plane hook 22 to contact the inner surface 48 of the hook 22. Then, when the bite plane 20 is slid into the channel 24, both the bite plane hook 22 and body 36 of the bite plane are securely anchored in the channel and the elastic band 16 is captured in the generally circular space 50 bounded by the inner surface 48 and the bottom wall 34 of the channel. The bite plane 20, therefore, is a combined means for separating the patient's maxilla and mandible, via the thickness of the bite plane 20, and for anchoring the elastic means which advances the mandible.

The preferred bands 16, 16' are elastic O-rings (FIG. 8), made available in a variety of diameters to create different lengths when stretched between the retention hooks 18, 18' and the bite plane hooks 22. Different bands of different lengths and thickness and different elasticities may be provided to satisfy the patient's needs. Preferably, the length of O-ring band 16 is about 15–30 mm from anterior end to posterior end, or about 30–60 mm in circumference. Preferably, but not necessarily, the O-rings are made of silicone or urethane and have a thickness of 1.5 mm and a durometer hardness of about 60–80 Shore A. This way, the band 16 has a firmer, more authoritative bias than is currently available from standard orthodontic elastics. Patient response has been very positive to embodiments of the subject invention with firm bands 16 with durometer hardness within this 60–80 Shore A range. We think this is because the firmer bias of these elastic bands encourages the patient's musculature to relax, and not to fight or resist the bias.

In FIGS. 7A–G are depicted detail views of embodiments of a bite plane 20 of the present invention, namely for vertical openings of about 6–14 mm. The bite planes 20 may be made of injection molded plastic. Based on the individual patient's needs, different bite planes may be substituted in place of the original bite planes, for example, ones that are thicker or thinner to further open or partially close the patient's bite, respectively. The recommended bite plane will be the thinnest one that will relieve the sleep apnea and/or snoring and still provide for maximum patient comfort. The bite planes are attached to the posterior occlusal right and left surfaces of the mandibular base 14. When it is desired to remove and replace bite plane 20 with a thicker or thinner bite plane, or to replace the elastics, one simply slides the bite plane 20 backwards out of the channel 24. Then, the elastic band 16 may be unhooked from the hook extension 22, a new bite plane or elastic selected, and the bite plane and elastic reconnected so that the bite plane with its captured elastic may be slid forward into the channel 24.

Although the slide-in, combination hook-bite-plane system of FIGS. 2, and 4–7 is preferred because of simplicity, cleanliness, and ease of manufacture, alternative embodiments may be used in the present invention. Other attachment means, besides the single, longitudinal channel may be used to attach the bite planes to the mandibular base. For example, channels besides the dove-tailed channel or a C-shaped channel may be used, as long as a wall of the channel extends inwardly or "overhangs" the bottom wall enough to capture at least a portion of the bite plane and a forward end of the channel system retains the bite plane. A plurality of channels capturing protrusions on the bottom of the bite plane may be used. Although the preferred channel is a separate member anchored to the lower base 14 by acrylic or other bonding method, the invention includes channels that are otherwise attached to or formed in the lower base, for example, cutting of a channel in excess lower base material so that the channel is an integral part of the lower base. Therefore, in the claims, the term "channel in the lower base" includes channel members that are attached to the lower base and also channels integrally formed in the lower base. Also, the term "a channel" having an "overhanging" or "inwardly-extending" wall may be a variety of designs shaped to capture the bite plane. Also, other attachment means for the bite planes, such as wire-attachment or temporary bonding are included as less-preferred embodiments of the invention.

By placing the mandibular connection points for the elastic bands on the bite plane members, the preferred embodiment eliminates the need for mandibular hooks that are separate from the bite planes. Other designs, however, are included in the invention, such as less-preferred embodiments that include retention hooks bonded to the buccal portions of the mandibular base, or embodiments that have non-elastic connection members between the upper and lower bases.

The elastic mandibular advancement appliance of the present invention is a removable oral device. It fits independently over the maxillary and mandibular dental arches, providing adjustable vertical mouth opening and variable anterior positioning of the mandible. The vertical opening is incrementally adjustable via interchangeable posterior occlusal bite planes. The anterior positioning of the mandible is accomplished by interchangeable urethane or silicone elastic bands, or standard orthodontic elastics, both of varying lengths and elasticity. This system allows for matching elastic pull to the opposing muscular forces. The elastic force may be increased, or decreased, in response to neuromuscular conditioning, or other factors. The appliance of the present invention provides medical and dental professionals with a non-surgical, non-invasive means of manipulating vertical and anterior positioning of the mandible as may be indicated in the treatment of Obstructive Sleep Apnea (OSA) and snoring. The adjustability of the elastic forces, and the freedom of lateral movement of the mandible, enables the appliance to give the patient comfort for the musculature and the temporomandibular joint heretofore unrealized.

The appliance of the present invention is fabricated using maxillary and mandibular thermal pressure formed plastic upper and lower bases to which two (2) injection molded plastic retention hooks are bonded with orthodontic acrylic and two (2) slide-in, removable bite planes are connected by cooperation with a channel. The appliance of the present invention is fabricated on a custom, per-patient basis. The components necessary for a preferred embodiment are listed below and may be offered in "kit" form for fabrication of the appliances in local labs and offices:

(1) Two 0.060 (about 1.5 mm) or 0.080 inch (about 2 mm) thick sheets of clear PETG (FDA & USP Class 6 approved) plastic cut to fit the various vacuum/pressure forming machines (typically 125 mm squares or circles). PETG is the currently preferred plastic, however, many different types of plastic are available, and certainly other types could work as well or better. Other beneficial plastic types may become available in the future, and are included in the scope of the invention.

(2) At least one set of two posterior occlusal bite planes having elastic band connection points and made of injection molded plastic, for placement in channels on the occlusal portion of the lower, or mandibular, section.

(3) Two channel members made of injection molded plastic, which are anchored to the lower base for slidably receiving the two posterior bite planes.

(4) Two elastic band retention hooks made of injection molded plastic, for attachment to the anterior of the maxillary section of the appliance by bonding with orthodontic cold-cure acrylic (standard for fabricating retainers and ADA certified).

(5) One or more pairs of O-ring bands or other elastics, the pairs having various sizes and elasticities.

The preferred method of fabricating and custom-fitting the elastic mandibular advancement appliance to the patient comprises an initial office visit, lab work, and one or more follow-up visits, as described below:

Initial Office Visit:

Obtain an upper (maxillary) and lower (mandibular) impression of the teeth and supporting soft tissue including the upper hard palate. This impression must be extremely accurate to avoid tooth soreness, and/or movement when the appliance is placed in the patient's mouth. The impression is taken by: (1) having the patient rinse with a pre-impression mouth wash, like Muco Sol™ for example, to eliminate any saliva distortion; (2) taking impressions that extend beyond the most posterior molar teeth; (3) pouring the impressions immediately to avoid distortion using a hard lab stone; (4) taking a wax bite with the patient biting in a true centric occlusion. The professional then sends the patient's models and wax bite to the lab.

Lab Process:
(1) The models are trimmed and mounted on a fixator, so the teeth are in their proper centric occlusion. The fixator is constructed so the models may be removed from and returned to the fixator with precision, while precisely maintaining the pre-set vertical opening and wax bite relation of the maxillary and mandibular models.
(2) The lab technician blocks out the undercuts on the models so the appliance will have the correct retention when inserted by the patient on the teeth.
(3) A clear sheet of 0.060 inch or 0.080 inch PETG plastic is placed in a thermo-pressure forming dental machine. The upper and then the lower models are placed on this machine and the plastic is pressure formed over the teeth and supporting soft tissues and palate of each model after the proper heat is applied to the plastic.
(4) The newly formed plastic trays or "bases" are trimmed while on the models. On the maxillary model the plastic is trimmed at the gingival margin on the labial and buccal surfaces, and extends transpalatal distal to the first or second molars leaving the palate completely covered with plastic sheet. On the mandibular model the plastic is trimmed at the gingival margin on the labial, buccal and lingual surfaces. The models, with their newly formed and trimmed plastic bases are then returned and secured to the fixator.
(5) Left and right channel members, preferably prefabricated by injection molding, are permanently attached to the mandibular plastic base by the following method: The exact location on the posterior occlusal mandibular surface where the right and left channel members are to be bonded is determined by measuring the distance from the maxillary elastic retention hooks on the maxillary base to the front of the right and left channel members, with upper and lower models mounted on the articulator. A mark is made on the lower tray at this distance with right and left distance equal. Dental acrylic is placed on the occlusal posterior surfaces of the mandibular tray, and the right and left channel members are immediately set in position on top of the uncured acrylic aligning the front of the channel members with the mark. Additional acrylic (if needed) is flowed around the channel members, and the lower (mandibular) model and base with channel members is cured. The additional step of inserting bite planes into the channel members and adjusting exact placement of bite planes into the channel members and adjusting exact placement of bite planes prior to the "setting up" of the acrylic may be preferred, and can be done prior to removing models from articulator. The lower (mandibular) model and base with bonded channel members is then cured in the pressure pot.
(6) On the upper, maxillary formed base, just in front of the cuspids, or canine teeth, an elastic band retention hook is bonded with clear orthodontic acrylic on each side, right and left. These retention hooks are to be placed preferably at the occlusion and equal distance, right and left, from the points at which the elastic bands are to be connected to the mandibular base, that is, the hook extension of the bite planes, or approximately at the front of the channel members. The upper (maxillary) model and base with bonded retention hooks is then cured in the pressure pot.
(7) The bases are then carefully removed from the models, polished and returned to the professional.

Second Office Visit:

The doctor or other professional positions a pair of selected elastic bands in the right and left hook extensions of a selected pair of bite planes, and slides the bite planes into the channel members of the lab's custom-made appliance. The bite planes supplied to the professional are made of an injection molded plastic which offers outstanding intra-oral characteristics, i.e., non-deforming, low coefficient of friction, etc.

The professional then tries in the elastic mandibular advancement appliance with thin bite planes in place, by inserting the upper and lower bases in the patient's mouth. Information is obtained from the patient as to any pressures on the teeth or gingiva. Also, the appliance is checked for comfort of and evenness of opening from side to side with the patient. If pressures are felt by the patient on any tooth or any area of the gingiva, then these areas must be carefully relieved. The only reasons there would be pressure on the teeth or gums are the following: (1) inaccurate impression; (2) warped model; or (3) tooth movement or dental work since the impression was taken.

When there is no pressure on teeth or gingiva, the elastics are engaged on the elastic retention hooks on each side. The proper size elastic band to advance the mandible 8 mm in the beginning may be used, unless the patient complains of discomfort.

On this second and any subsequent office visits, the professional may adjust the vertical separation of the maxilla and mandible or adjust the forward advancement of the mandible, as he/she sees fit, based on the individual patient's needs, facial and jaw formation, and the professional's experience. To accomplish this, the professional or the patient may simply remove the appliance, slide out the bite planes, and replace the elastic bands, and/or the bite planes, with those of different size/elasticity or thickness, respectively. The feature of having the bite plane serve as both bite-opening means and band connection-means, and the feature of the bite plane being slidably insertable and removable makes office visits and every-day use efficient and trouble-free.

In summary, the elastic mandibular advancement appliance is a removable mandibular advancement, or repositioning, appliance which uses elastic bands to pull the mandible forward. By its design, the elastic mandibular advancement appliance maintains infinite adjustability (by doctor or patient). The elastic mandibular advancement appliance may be worn with the mandible not advanced (without bands) or advanced any percent of its maximum movement. By increasing the force of the elastics, the mandible is gently pulled forward to a position which increases the opening of the airway at the base of the tongue for increased air flows. The mandible is preferably pulled forward just enough to significantly reduce or stop snoring, which is vibration of soft tissues within the pharyngeal airway, and to significantly reduce or stop sleep apnea, which is the tongue falling back against the pharynx and stopping air flow.

The elastic mandibular advancement appliance never advances the mandible to a "fixed" position, unlike other appliances, due to the forgiving nature of elastics. Balance between right and left side muscles and right and left side temporomandibular joints remains flexible at all times, allowing the patient to seek the most comfortable, natural position while the elastic mandibular advancement appliance is worn. In contrast to other appliances in this art, the elastic mandibular advancement appliance is of minimal bulk. Also, patient acceptance in clinical trials has been high.

In summary, the elastic mandibular advancement appliance of the present invention is set apart by its use of elastics—yielding a completely adjustable, forgiving appliance, which is in many ways far more comfortable then anything else available. The present invention is also set apart by its simple, easy-to-adjust, and comfortable design, having a slide-in, combination hook-bite-plane system. Therapeutically, by being able to increase or decrease the force exerted on the mandible, and by being able to adjust the bite opening, the doctor or patient may fine tune the elastic mandibular advancement appliance at any time to achieve the desired results.

Although this invention has been described above with reference to particular means, materials and embodiments, it is to be understood that the invention is not limited to these disclosed particulars, but extends instead to all equivalents within the scope of the following claims.

What is claimed is:

1. An oral appliance comprising:
   a. an upper base conforming to a patient's maxillary dentition and soft tissues, said upper base having an anterior portion and a posterior portion;
   b. a lower base conforming to the patient's mandibular dentition and soft tissues, said lower base having an anterior portion and a posterior portion, and the lower base posterior portion having right and left occlusal surfaces;
   c. right and left occlusal bite planes, for opening the patient's bite, each bite plane having a body with a top occlusal surface and a bottom anchoring portion; and
   d. means on the body and anchoring portions for removably attaching said right and left bite planes to the right and left occlusal surfaces of one of the bases, said means comprising right and left channels in the ends of said one base for slidably receiving and capturing the anchoring portions of the right and left bite planes, respectively, means on each bite plate and the one base to which the ends of flexible bands may be releasably attached, the attachment means on the upper base being forward of the attachment means on the lower base, so that, when the ends of bands of desired length and/or elasticity, are attached thereto, and the bases are fitted over the patient's teeth, the lower base and thus, the patient's lower jaw are advanced forwardly.

2. The appliance of claim 1, wherein the attachment means comprises right and left channel members bonded to the one base and each having a channel for receiving and capturing the bite plane anchoring portion.

3. The appliance of claim 1, wherein the attachment means comprises right and left channels integrally formed in the posterior portion occlusal surfaces of the one base.

4. The appliance of claim 1, wherein the channels each comprise an open end for slidably receiving the anchoring portion of the bite plane, and two inwardly-extending dovetail sidewalls for capturing the bite plane anchoring portion.

5. The appliance of claim 1, wherein the bite planes are replaceable with other bite planes of different thickness.

6. An oral mandibular advancement appliance comprising:
   a. an upper base conforming to a patient's maxillary dentition and soft tissues, said upper base having an anterior portion and a posterior portion;
   b. a lower base conforming to the patient's mandibular dentition and soft tissues, said lower base having an anterior portion and a posterior portion, and the lower base posterior portion having right and left occlusal surfaces;
   c. right and left occlusal bite planes, for opening the patient's bite, each bite plane having a body with a top occlusal surface and a bottom anchoring portion;
   d. means for removably attaching said right and left bite planes to the right and left occlusal surfaces of said lower base, said means comprising right and left channels in said lower base for slidably receiving and capturing the anchoring portions of the right and left bite planes, respectively;
   e. means, extending between the anterior portion of the upper base and the posterior portion of the lower base, for pulling said lower base forward relative to said upper base to advance the patient's mandible.

7. The appliance of claim 6, wherein the channels each comprise an open end for slidably receiving the anchoring portion of the bite plane, and two inwardly-extending sidewalls for capturing the bite plane anchoring portion.

8. The appliance of claim 6, wherein the bite planes are replaceable with other bite planes of different thickness.

9. The appliance of claim 6, wherein the means for pulling the lower base forward comprises a flexible member and means for connecting ends of the flexible member to the upper base anterior portion and to the lower base posterior portion.

10. The appliance of claim 9, wherein the flexible member comprises an elastic O-ring.

11. The appliance of claim 9, wherein the means for connecting the flexible member to the upper base anterior portion comprises a retention hook on an occlusal surface of the anterior portion of the upper base.

12. The appliance of claim 9, wherein the means for connecting the flexible member to the lower base anterior portion comprises a hook extending from the front end of the body of each of said bite planes.

13. The appliance of claim 12, wherein the opposite sides of said bite plane hook are slidably captured in said channel.

14. The appliance of claim 6, wherein the means for pulling the lower base forward is non-elastic.

15. An oral appliance comprising:
   a. an upper base conforming to a patient's maxillary dentition and soft tissues, said upper base having an anterior and a posterior portion,
   b. a lower base conforming to the patient's mandibular dentition and soft tissues, said lower base having an anterior and a posterior portion and said lower base posterior portion having right and left occlusal surfaces; and
   c. right and left occlusal bite planes attached to the posterior portion of the lower base, wherein said bite planes occlude with the upper base to vertically distance the upper and lower bases to the patient's bite, each bite plane comprising a body having a top occlusal surface, front end, and a hook extending forwardly from the front end.

16. The appliance of claim 15, further comprising an attachment means for removably attaching said bite planes to said posterior portion of the lower base.

17. The appliance of claim 15, further comprising a connection member extending between the upper and lower base, and means for connecting said connection member to the upper base and to the lower base.

18. The appliance of claim 17, wherein the means for connecting said connection member to the lower base comprises said bite plane hook.

19. The appliance of claim 18, wherein the means for connecting the connection member to the upper base comprises a retention hook attached to an occlusal surface of the anterior portion of the upper base.

20. The appliance of claim 18 wherein the connection member comprises flexible band means releasably connected to the connection means on the upper base and said bite plane hook.

21. The appliance of claim 17, wherein the connection member extends between the occlusal anterior portion of the upper base and the occlusal posterior portion of the lower base, for pulling said lower base forward relative to said upper base to advance the patient's mandible.

22. An oral appliance, comprising upper and lower trays adapted to fit tightly but removably over the occlusal surfaces of the upper and lower teeth of a patient, a bite plane on the occlusal surface of both sides of one tray each having a bite surface which protrudes therefrom so as to engage the occlusal surfaces on the other tray and thus maintain the occlusal surfaces of the trays in predetermined spaced relation, when the trays are so fitted, a pair of flexible bands, and means for releasably attaching the ends of each band to the anterior and the posterior portions of each opposite side of the upper and lower trays, respectively, each band being of such length and/or elasticity, that, when its ends are so attached, and the trays are fitted over the patient's teeth, the lower tray and thus the patient's lower jaw are advanced forwardly with respect to the upper tray and jaw, said attaching means including a hook on the end of the bite plane of one tray which faces the attachment means on the other tray and over which the end of a band may be placed for extension from opposite open ends of the hook and the outer sides of the bite plane of said one tray so that, upon attachment of the opposite end of said band to the attaching means on the other tray, the sides of the band are disposed intermediate occlusal surfaces of the trays.

23. An oral appliance as in claim 23, wherein each bite plane is removably mounted on the one tray.

24. An oral appliance as in claim 23, wherein the one tray is the lower tray.

25. An oral appliance as in claim 23, wherein each one tray has means on its occlusal surfaces forming a channel which is open at one end, and each bite plane has means on opposite sides of the open ends of the hook to fit tightly within sides of the channel for releasably anchoring the bite plate to the tray.

* * * * *